United States Patent [19]
Jachow et al.

[11] Patent Number: 6,074,472
[45] Date of Patent: Jun. 13, 2000

[54] HYDROLYTIC PREPARATION OF TITANIUM DIOXIDE PIGMENTS

[75] Inventors: Harald Jachow, Bensheim; Ekkehard Schwab, Neustadt; Claudius Kormann, Schifferstadt; Wilma Dausch, Limburgerhof; Karin Sperling, Neustadt; Horst Westenfelder, Neustadt, all of Germany

[73] Assignee: BASF Aktiengesellschaft, Germany

[21] Appl. No.: 09/011,608

[22] PCT Filed: Aug. 8, 1996

[86] PCT No.: PCT/EP96/03504

§ 371 Date: Feb. 12, 1998

§ 102(e) Date: Feb. 12, 1998

[87] PCT Pub. No.: WO97/07058

PCT Pub. Date: Feb. 27, 1997

[30] Foreign Application Priority Data

Aug. 19, 1995 [DE] Germany ............ 195 30 574

[51] Int. Cl.⁷ .................................. C01B 23/047
[52] U.S. Cl. .................. 106/436; 106/437; 423/610; 423/611; 423/615; 423/616
[58] Field of Search .......... 423/610, 611, 423/615, 616; 106/436, 437, 438, 439, 440, 441, 442, 443; 424/401, 59, 600

[56] References Cited

U.S. PATENT DOCUMENTS

| | | | |
|---|---|---|---|
| 3,898,321 | 8/1975 | Marsh | 423/615 |
| 4,073,877 | 2/1978 | Klein et al. | 423/616 |
| 5,453,267 | 9/1995 | Kemp et al. | 106/436 |
| 5,468,471 | 11/1995 | Zecchino et al. | 424/59 |
| 5,643,557 | 7/1997 | Eteve et al. | 424/59 |
| 5,658,555 | 8/1997 | Ascione et al. | 424/59 |
| 5,695,747 | 12/1997 | Forestier et al. | 424/59 |
| 5,733,895 | 3/1998 | Forestier et al. | 423/608 |

FOREIGN PATENT DOCUMENTS

| | | |
|---|---|---|
| 2219117 | 9/1974 | France . |
| 2435955 | 7/1974 | Germany . |
| 2206339 | 1/1989 | United Kingdom . |

OTHER PUBLICATIONS

*Chem. Abst.,* vol. 116, No. 2, Jan. 13, 1992, Abst. No. 847&v, p. 108.

*Romp Chemie Lexicon,* 9 Edition, Thieme Verlag, 1992, p. 4630.

*Romp Chemie Lexicon,* 9 Edition, Thieme Verlag, 1992, p. 4804.

*Romp Chemie Lexicon,* 9 Edition, Thieme Verlag, 1992, p. 4213.

*Primary Examiner*—C. Melissa Koslow
*Attorney, Agent, or Firm*—Keil & Weinkauf

[57] ABSTRACT

Titanium dioxide pigments are obtainable by complete hydrolysis of a hydrolyzable titanium compound at from 0 to 100° C. with intensive stirring and with setting of a pH in the range from 3 to 8 and maintenance of this pH within a range of 0.3 units.

The titanium dioxide pigments can be employed for the production of cosmetic preparations and medicaments.

2 Claims, No Drawings

HYDROLYTIC PREPARATION OF TITANIUM DIOXIDE PIGMENTS

The present invention relates to titanium dioxide pigments, obtainable by complete hydrolysis of a hydrolyzable titanium compound at from 0 to 100° C. with intensive stirring and with setting of a pH in the range from 3 to 8 and maintenance of this pH within a range of 0.3 units.

The invention further relates to such titanium dioxide pigments coated with a physiologically tolerable inorganic compound reducing the photo effect of titanium dioxide, to a process for the preparation of such uncoated and coated titanium dioxide pigments, to their use for cosmetic and medicinal purposes, to cosmetic preparations and essentially anhydrous dispersions which comprise such coated and uncoated titanium dioxide pigments, and to a process for the preparation of such dispersions.

The use of titanium dioxide pigments in cosmetics, in particular sunscreen compositions, is generally known, for example from Römpp Chemie Lexikon (Römpp's Chemical Encyclopedia), 9th Edition, Thieme Verlag, Stuttgart/New York, 1992, p. 4630.

Sunscreen compositions are generally understood as meaning compositions for the protection of the human skin from harmful effects of solar radiation, in particular of ultraviolet radiation (UV), which is subdivided according to its biological action into the ranges UV-A (wavelength 400–320 nm), UV-B (320–280 nm) and UV-C (280–200 nm) (Römpp, loc. cit., p. 4804). A sunscreen composition specifically has the task of allowing the UV-A responsible for the tanning of the skin to pass unchanged and, on the other hand, of stopping the UV-B, which can cause skin damage; UV-C, however, is absorbed in the atmosphere to the greatest possible extent (Römpp, loc. cit., p. 4213).

The preparation of titanium dioxide pigments suitable as sunscreen compositions is generally known, for example from GB-A 2206339.

To this end, ilmenite ($FeTiO_3$) is decomposed using concentrated sulfuric acid, the decomposition cake is dissolved in water and the iron(III) present is reduced chemically to iron(II). After a crystallization and filtration step, the solution is concentrated under reduced pressure and then hydrolyzed in the presence of heat to precipitate the titanium dioxide. After the neutralization of the solution with sodium hydroxide solution, the titanium dioxide is filtered off and washed with water.

After a wet milling of the titanium dioxide, the pigments can be coated, if desired, with an inorganic compound. The product is then dried at 110° C.

The pigments can be suspended in numerous solvents with the aid of dispersants and high-speed ball mills.

Pigments of this type are indeed suitable for sunscreen compositions; however, they have an undesirably high UV-A absorption compared with the desired UV-B absorption and a low transparency in the visible light range.

It is an object of the present invention to prepare titanium dioxide pigments which have, compared with a desirable UV-B absorption, a low UV-A absorption and high transparency in the visible light range, in a technically simple and cost-effective manner.

We have found that this object is achieved by the titanium dioxide pigments defined at the outset.

The titanium dioxide pigments can be obtained by complete hydrolysis of hydrolyzable titanium compounds. Suitable hydrolyzable titanium compounds are organic compounds such as complex compounds, for example titanyl acetylacetonate and titanocene dichloride, titanic acid esters, for example titanium methoxide, titanium ethoxide, titanium propoxide, titanium isopropoxide, titanium butoxide and titanium cresoxide, and also organic titanium salts, for example titanium stearate and titanium oxalate, and preferably inorganic compounds such as titanyl sulfate, titanium fluoride, titanium bromide, titanium iodide and, in particular, titanium tetrachloride or mixtures of such compounds. Compounds of this type are known.

During the hydrolysis, according to the invention a pH of from 3 to 8, in particular from 3 to 5, measured with a glass electrode, is maintained, where the pH during the hydrolysis reaction should vary according to the invention at most within a range, based on the maximum and the minimum value, of 0.3, preferably 0.2, units.

The desired pH of the reaction mixture can be set in a manner known per se by addition of acids, bases or buffer systems and kept within the range according to the invention.

Suitable bases are alkali solutions such as sodium hydroxide solution and ammonia solution or solutions of basic salts such as sodium carbonate and potassuim carbonate, and suitable acids are, in particular, mineral acids such as hydrochloric acid and sulfuric acid.

The hydrolysis can advantageously be carried out with water on its own or with a mixture of water and a water-miscible liquid diluent. Suitable liquid diluents are water-soluble alcohols such as ethanol and methanol and water-soluble ethers, in particular cyclic ethers, such as tetrahydrofuran and dioxane.

The reaction is generally carried out at from 0 to 100° C., preferably 10 to 30° C., with intensive stirring, whereby reaction times of from 1 to 25 hours result.

Other inorganic compounds can then be applied to the titanium dioxide pigments. If the coated titanium dioxide pigments are to be used for medicinal or cosmetic purposes, suitable compounds are, in particular, physiologically tolerable inorganic compounds reducing the photo effect of titanium dioxide, such as water-containing oxides or phosphates of aluminum, boron, silicon, zinc, iron, zirconium and cerium, alkali metal or alkaline earth metal borates, and mixtures of such compounds, which can be applied by known processes such as precipitation in amounts of from 0.1 to 50% by weight, based on the total pigment weight.

To remove the by-products formed during the preparation of the titanium dioxide pigments, a purification step is recommended, which can be carried out in a manner known per se, for example by filtration and subsequent washing.

The coated and uncoated titanium dioxide pigments can be isolated from the water-containing suspension by known methods, eg. by filtration and drying, or advantageously employed for the preparation of the essentially anhydrous dispersions mentioned at the outset.

The titanium dioxide pigments obtainable according to the invention have a particularly advantageous mean particle size (primary particles) for cosmetic purposes of from 3 to 8 nm, in particular 3 to 5 nm, and a specific surface area according to DIN 66132, measured using a Ströhlein areameter (Ströhlein, Düsseldorf) by the single point difference process according to Haul and Dümbgen, of from 200 to 400 $m^2/g$, preferably 250 to 350 $m^2/g$, and can be present, measured by electron diffraction, in amorphous form or in a crystalline form essentially consisting of anatase.

For the preparation of the dispersions comprising the titanium dioxide pigments, the pigments or the water-containing suspensions are mixed with a nonaqueous diluent and, if desired, additives.

Suitable nonaqueous diluents are oils, in particular physiologically acceptable oils, for example fatty alcohols, fatty acids such as oleic acid, fatty acid esters such as isopropyl palmitate, isopropyl stearate, isopropyl laurate and isopropyl myristate, vegetable oils such as sunflower oil, jojoba oil, groundnut oil, almond oil, avocado oil, macadamia nut oil, maize germ oil and castor oil, mineral oils such as liquid paraffins, benzoic acid esters, in particular $C_{12}$–$C_{15}$-alkyl benzoates, and also oligoglycerol esters such as caprylic acid triglyceride.

Suitable additives are primarily dispersing auxiliaries such as neutral or acidic phosphoric acid esters or their salts, for example diceteareth-10-phosphoric acid esters, triceteareth-4-phosphate and trilaureth-4-phosphate, primary, secondary, tertiary and quaternary ammonium compounds, for example cetyldimethyl-2-hydroxyethylammonium dihydrogenphosphate, polyacrylates, carboxylic acids and hydroxycarboxylic acids and their salts, esters, in particular with sorbitol or glycerol, for example polyoxyethylene-20-sorbitol fatty acid esters, metal alkoxides, alkanolamines and silicones.

If the aqueous suspension was employed for the preparation of the dispersions, the water content of the dispersion can be lowered further by known processes such as distillation, so that virtually anhydrous, in particular oily, dispersions can be obtained.

Dispersions of this type are of particular importance in the production of cosmetic preparations and medicaments.

To this end, further substances, in particular stabilizers such as magnesium salts and aluminum salts of fatty acids, complexing agents such as ethylenediaminetetraacetate (EDTA), antioxidants such as α-tocopherol and cosmetic active compounds such as panthenol, bisabolol, α-tocopherol, α-tocopherol acetate, aloe vera, algae extract and hyaluronic acid can be added to the dispersions in a manner known per se.

The titanium dioxide pigments, dispersions, cosmetic preparations and medicaments according to the invention are distinguished by a low UV-A absorption in relation to the UV-B absorption and high transparency in the visible light range, expressed by the ratio of the extinction coefficient in the UV-A or visible range to the extinction coefficient in the UV-B range.

The extinction coefficient is defined here by the following equation:

$$A = \epsilon \times C \times L$$

in which A is extinction, where $A = \ln I/I_0$ where I is intensity of the light after passage through the sample $I_0$ is intensity of the incident light $\epsilon$ is the extinction coefficient [l/g·cm], in each case based on the wavelength of the light given in brackets C is the concentration of titanium dioxide [g/l] and L is the path length [cm].

For the three ranges, measurements were made using a UV-VIS spectrometer (HP 8452, Hewlett-Packard) at the following wavelengths:

Visible light: 400 nm

UV-A range: 380 nm

UV-B range: 308 nm.

The ratio $\epsilon(308)/\epsilon(380)$ and $\epsilon(308)/\epsilon(400)$ is used here as a measure of a high UV-B absorption compared with the UV-A and visible range.

EXAMPLE 1

380 g of titanium tetrachloride and 1000 ml of sodium hydoxide solution (NaOH content 320 g/l) were added synchronously at a pH of 3 to 3800 g of water with intensive stirring at 20° C. in the course of 60 min and the mixture was then stirred for a further 30 min. A pH of 8 was set with intensive stirring using 25% strength by weight sodium hydroxide solution and the mixture was stirred for a further 30 min.

After filtering off the solid, the filter cake was washed with 9 l of distilled water.

The titanium dioxide pigments dried at 100° C./20 mbar had a mean particle size of 5 nm and a specific surface area of 253 m²/g.

A solution of 83.7 g of cetyldimethyl-2-hydroxyethylammonium dihydrogenphosphate in 195.3 g of water was added to 461 g of the filter cake, which had a titanium dioxide content of 21.1% by weight. After intensive stirring for 30 min, 400 g of caprylic acid triglyceride were added, after which the water was distilled off at 80° C./40–50 mbar.

The extinction coefficients listed in Table 1 were determined on a sample diluted with further caprylic acid triglyceride to a solids content of 50 mg/l.

EXAMPLE 2

760 g of titanium tetrachloride and 2000 ml of sodium hydroxide solution (NaOH content 320 g/l) were added synchronously at a pH of 3 to 3800 g of water with intensive stirring at 20° C. in the course of 120 min, and the mixture was stirred at 100° C. for a further 90 min. A pH of 8 was then set at 20° C. with intensive stirring using 25% strength by weight sodium hydroxide solution and the mixture was stirred at 20° C. for 30 min.

After filtering off the solid, the filter cake was washed with 9 l of distilled water.

The titanium dioxide pigments dried at 100° C./20 mbar had a mean particle size of 5 nm and a specific surface area of 286 m²/g.

A solution of 35.3 g of cetyldimethyl-2-hydroxyethylammonium dihydrogenphosphate in 82.3 g of water was added to 333.2 g of the filter cake, which had a titanium dioxide content of 26.5% by weight. After intensive stirring for 30 min, 233 g of caprylic acid triglyceride were added, after which the water was distilled off at 80° C./40–50 mbar.

The extinction coefficients listed in Table 1 were measured on a sample diluted as described in Example 1.

EXAMPLE 3

380 g of titanium tetrachloride and 1000 ml of sodium hydroxide solution (NaOH content 320 g/l) were added synchronously at a pH of 5 to 3800 g of water with intensive stirring at 20° C. in the course of 90 min. The mixture was then stirred for 30 min, and 180 ml of an aqueous solution of $Al_2(SO_4)_3 \cdot 18\ H_2O$ (content: 666.4 g/l) were added with intensive stirring in the course of 15 min. During the course of this, a pH of 5 was constantly maintained using 40 ml of sodium hydroxide solution (NaOH content 320 g/l). A pH of 8 was then set using 25% strength by weight sodium hydroxide solution and the mixture was stirred for a further 30 min.

After filtering off the solid, the filter cake was washed with 11 l of distilled water.

The titanium dioxide pigments dried at 100° C./20 mbar had a mean particle size of 5 nm and a specific surface area of 296 m²/g.

97.1 g of Hostaphat KL 340 N (Hoechst AG) and 246 g of caprylic acid triglyceride were added to 1000 g of the filter cake, which had a solids content of 16.4% by weight, the solid consisting to 78.4% by weight of titanium dioxide, and the mixture was intensively stirred for 8 hours, after which the water was distilled off at 70° C./40–50 mbar.

The extinction coefficients listed in Table 1 were measured on a sample diluted as described in Example 1.

TABLE 1

| Sample | $\epsilon(308)$ | $\epsilon(380)$ | $\epsilon(400)$ | $\epsilon(308)/\epsilon(380)$ | $\epsilon(308)/\epsilon(400)$ |
| --- | --- | --- | --- | --- | --- |
| Ex. 1 | 30.1 | 13.9 | 12.1 | 2.17 | 2.49 |
| Ex. 2 | 34.0 | 18.2 | 15.8 | 1.87 | 2.15 |
| Ex. 3 | 36.3 | 15.3 | 14.0 | 2.37 | 2.59 |

We claim:

1. A process for preparing a titanium oxide pigment having a mean particle size of from 3 to 8 nm coated with an insoluble physiologically tolerated inorganic compound, which process comprises the steps of completely hydrolyzing a hydrolyzable titanium compound at a pH in the range of from 3 to 8 and at a temperature in the range of from 10 to 30° C., where the pH does not vary by more than 0.3 units during the hydrolyzing process, to produce titanium dioxide pigment, and subsequently precipitating the inorganic compound on the titanium dioxide pigment.

2. A process for preparing an anhydrous dispersion comprising a titanium oxide pigment having a mean particle size of from 3 to 8 nm coated with an insoluble physiologically tolerated inorganic compound, which process comprises the steps of completely hydrolyzing a hydrolyzable titanium compound at a pH in the range of from 3 to 8 and at a temperature in the range of from 10 to 30° C., where the pH does not vary by more than 0.3 units during the hydrolyzing process, to produce titanium dioxide pigment, optionally coating the titanium dioxide pigment with the inorganic compound, and subsequently dispersing the titanium dioxide pigment in a nonaqueous liquid diluent.

* * * * *